United States Patent
Matusz

(10) Patent No.: US 9,018,126 B2
(45) Date of Patent: Apr. 28, 2015

(54) EPOXIDATION CATALYST, A PROCESS FOR PREPARING THE CATALYST, AND A PROCESS FOR THE PRODUCTION OF AN OLEFIN OXIDE

(75) Inventor: Marek Matusz, Houston, TX (US)

(73) Assignee: Shell Oil Company, Houston, TX (US)

( * ) Notice: Subject to any disclaimer, the term of this patent is extended or adjusted under 35 U.S.C. 154(b) by 516 days.

(21) Appl. No.: 13/179,729

(22) Filed: Jul. 11, 2011

(65) Prior Publication Data

US 2012/0016143 A1    Jan. 19, 2012

Related U.S. Application Data

(60) Provisional application No. 61/363,731, filed on Jul. 13, 2010.

(51) Int. Cl.
| | | |
|---|---|---|
| *B01J 31/00* | (2006.01) | |
| *B01J 27/24* | (2006.01) | |
| *B01J 27/25* | (2006.01) | |
| *B01J 27/043* | (2006.01) | |
| *B01J 27/049* | (2006.01) | |
| *B01J 27/047* | (2006.01) | |
| *B01J 27/051* | (2006.01) | |
| *B01J 27/055* | (2006.01) | |
| *B01J 27/185* | (2006.01) | |
| *B01J 21/00* | (2006.01) | |
| *B01J 21/02* | (2006.01) | |
| *B01J 23/00* | (2006.01) | |

(Continued)

(52) U.S. Cl.
CPC ............... *B01J 23/892* (2013.01); *B01J 21/04* (2013.01); *B01J 23/8946* (2013.01); *B01J 23/8986* (2013.01); *B01J 35/1009* (2013.01); *B01J 35/1038* (2013.01); *B01J 35/109* (2013.01); *B01J 37/0203* (2013.01); *B01J 37/0213* (2013.01); *C07D 301/10* (2013.01)

(58) Field of Classification Search
USPC ......... 502/161, 200, 201, 204, 206, 207, 213, 502/218–222, 315, 317, 321, 326, 330, 337, 502/344
See application file for complete search history.

(56) References Cited

U.S. PATENT DOCUMENTS

| | | | |
|---|---|---|---|
| 4,242,235 A | 12/1980 | Cognion et al. | ............... 252/455 |
| 4,740,493 A | 4/1988 | Boehning et al. | ............. 502/348 |

(Continued)

FOREIGN PATENT DOCUMENTS

| | | | | |
|---|---|---|---|---|
| EP | 3642 | 8/1979 | ........... | C07D 301/10 |
| WO | WO0015333 | 3/2000 | ............... | B01J 23/50 |

OTHER PUBLICATIONS

Wang, F. F. Y. (Ed.), "Treatise on Materials Science and Technology", vol. 9, (New York, 1976), pp. 79-81.

(Continued)

*Primary Examiner* — Cam N. Nguyen

(57) ABSTRACT

A catalyst for the epoxidation of an olefin comprising a carrier and deposited on the carrier, silver, a promoting amount of one or more promoters selected from the group consisting of alkali metals and rhenium and a promoting amount of nickel, wherein the nickel is added as a nickel compound or nickel complex during the initial impregnation along with the silver and other promoters; including a process for preparing the catalyst; a process for preparing an olefin oxide by reacting a feed comprising an olefin and oxygen in the presence of the catalyst; and a process for preparing a 1,2-diol, a 1,2-diol ether, a 1,2-carbonate, or an alkanolamine.

9 Claims, 1 Drawing Sheet

(51) Int. Cl.
  *B01J 23/02* (2006.01)
  *B01J 23/04* (2006.01)
  *B01J 23/40* (2006.01)
  *B01J 23/42* (2006.01)
  *B01J 23/58* (2006.01)
  *B01J 23/89* (2006.01)
  *B01J 35/10* (2006.01)
  *B01J 37/02* (2006.01)
  *C07D 301/10* (2006.01)
  *B01J 21/04* (2006.01)

(56) References Cited

U.S. PATENT DOCUMENTS

| | | | | |
|---|---|---|---|---|
| 4,766,105 | A | 8/1988 | Lauritzen | 502/216 |
| 4,822,900 | A | 4/1989 | Hayden | 549/534 |
| 4,845,296 | A | 7/1989 | Ahmed et al. | 564/477 |
| 5,100,859 | A | 3/1992 | Gerdes et al. | 502/439 |
| 5,145,824 | A | 9/1992 | Buffum et al. | 502/216 |
| 5,380,697 | A | 1/1995 | Matusz et al. | 502/348 |
| 5,380,885 | A | 1/1995 | Kemp | 594/536 |
| 5,384,302 | A | 1/1995 | Gerdes et al. | 502/439 |
| 5,512,530 | A | 4/1996 | Gerdes et al. | 502/351 |
| 5,733,842 | A | 3/1998 | Gerdes et al. | 502/439 |
| 5,739,075 | A * | 4/1998 | Matusz | 502/302 |
| 5,801,259 | A | 9/1998 | Kowaleski | 549/536 |
| 6,040,467 | A | 3/2000 | Papavassiliou et al. | 549/534 |
| 6,080,897 | A | 6/2000 | Kawabe | 568/858 |
| 6,368,998 | B1 | 4/2002 | Lockemeyer | 502/347 |
| 7,247,600 | B2 * | 7/2007 | Lockemeyer | 502/347 |
| 7,507,577 | B2 | 3/2009 | Tung | 435/290.2 |
| 7,507,845 | B1 | 3/2009 | Gueckel | 549/536 |
| 7,713,903 | B2 * | 5/2010 | Lockemeyer et al. | 502/202 |
| 7,714,152 | B2 | 5/2010 | Pak | 549/536 |
| 8,546,294 | B2 * | 10/2013 | Liu et al. | 502/241 |
| 2002/0143197 | A1 * | 10/2002 | Lockemeyer | 549/534 |
| 2005/0085380 | A1 * | 4/2005 | Lockemeyer | 502/243 |
| 2007/0207914 | A1 * | 9/2007 | Lockemeyer | 502/11 |
| 2008/0081920 | A1 | 4/2008 | Gueckel | 549/533 |
| 2008/0281118 | A1 * | 11/2008 | Matusz | 558/260 |
| 2009/0131695 | A1 | 5/2009 | Gerdes et al. | 549/534 |
| 2009/0177016 | A1 | 7/2009 | Lockemeyer et al. | 568/680 |
| 2009/0198076 | A1 | 8/2009 | Gueckel | 549/536 |
| 2010/0191006 | A1 * | 7/2010 | Gueckel | 549/536 |
| 2010/0280261 | A1 * | 11/2010 | Howard et al. | 549/230 |
| 2011/0152073 | A1 * | 6/2011 | Dialer et al. | 502/347 |
| 2012/0226058 | A1 * | 9/2012 | Pak et al. | 549/536 |

OTHER PUBLICATIONS

Reed, J. S., "Introduction to the Principles of Ceramic Processing", (New York, 1988), pp. 152 ff.
"Kirk-Othmer Encyclopedia of Chemical Technology", 4th edition, vol. 5, pp. 610 ff, (1993).
"Kirk-Othmer Encyclopedia of Chemical Technology", 3rd edition, vol. 9, 1980, pp. 445-447.

* cited by examiner

EPOXIDATION CATALYST, A PROCESS FOR PREPARING THE CATALYST, AND A PROCESS FOR THE PRODUCTION OF AN OLEFIN OXIDE

This application claims priority to U.S. Provisional Application No. 61/363,731, filed on Jul. 13, 2010, which is herein incorporated by reference.

FIELD OF THE INVENTION

The present invention relates to an epoxidation catalyst, a process for preparing the catalyst, and a process for the production of an olefin oxide, a 1,2-diol, a 1,2-diol ether, a 1,2-carbonate, or an alkanolamine.

BACKGROUND OF THE INVENTION

In olefin epoxidation, a feed containing an olefin and oxygen is contacted with a catalyst under epoxidation conditions. The olefin is reacted with oxygen to form an olefin oxide. A product mix results that contain olefin oxide and, typically, unreacted feed and combustion products.

The olefin oxide may be reacted with water to form a 1,2-diol, with carbon dioxide to form a 1,2-carbonate, with an alcohol to form a 1,2-diol ether, or with an amine to form an alkanolamine. Thus, 1,2-diols, 1,2-carbonates, 1,2-diol ethers, and alkanolamines may be produced in a multi-step process initially comprising olefin epoxidation and then the conversion of the formed olefin oxide with water, carbon dioxide, an alcohol, or an amine.

Olefin epoxidation catalysts typically comprise a silver component, usually with one or more additional elements deposited therewith, on a carrier. U.S. Pat. No. 4,766,105 discloses an ethylene oxide catalyst comprising silver, alkali metal, rhenium and a rhenium co-promoter selected from sulfur, molybdenum, tungsten, chromium and mixtures thereof supported on a carrier. The ethylene oxide catalyst described in U.S. Pat. No. 4,766,105 provides an improvement in one or more catalytic properties.

The catalyst performance may be assessed on the basis of selectivity, activity and stability of operation. The selectivity is the fraction of the converted olefin yielding the desired olefin oxide. As the catalyst ages, the fraction of the olefin converted normally decreases with time and to maintain a constant level of olefin oxide production the temperature of the reaction may be increased.

The selectivity determines to a large extent the economical attractiveness of an epoxidation process. For example, one percent improvement in the selectivity of the epoxidation process can substantially reduce the yearly operating costs of a large scale ethylene oxide plant. Further, the longer the activity and selectivity can be maintained at acceptable values, the longer the catalyst charge can be kept in the reactor and the more product is obtained. Quite modest improvements in the selectivity, activity, and maintenance of the selectivity and activity (i.e., stability) over long periods yield substantial dividends in terms of process efficiency.

In addition, since ethylene oxide catalysts have a limited commercial life (typically 1 to 2 years) the catalyst needs to be exchanged for a fresh batch at that time resulting in lost plant production. Also replacement of the catalyst is expensive as the raw materials like silver are expensive. Extending catalyst life is therefore very attractive from the economic point of view.

One of the reasons for activity and selectivity decline is loss of silver surface area by the mechanism of silver sintering. Eliminating or slowing down silver sintering would extend economic life of the catalyst. This reduction in silver sintering is what can be achieved by practice of the presently claimed invention.

SUMMARY OF THE INVENTION

It has now been discovered that depositing nickel salts on silver catalysts during the initial impregnation results in low silver sintering rates and, therefore, much improved stability. The amount of nickel salt deposited should be catalytic, that is in the amount showing the effect on silver sintering. Larger amounts will show a larger effect. Nickel can be deposited in the form of salts, complexes and such, but it is believed that during catalyst drying and heating step it is decomposed to oxides. Nickel is not believed to be present in the metallic state.

The principle of decreased sintering was shown by heating a sample of the catalyst in air at 600° C. for some time and examining SEM (Scanning Electron Microscopy) photographs. It is a well known principle that the presence of an oxidative atmosphere and high temperature accelerates silver sintering. The examination of SEM images can be done by visual inspection, where more stable catalyst will show a presence of small silver particles, and less stable catalyst will show a presence of large silver particles. A more rigorous analysis of particle size distribution can also be performed.

As shown in the examples which follow, a normal prior art catalyst comprising 8 wt % silver on alpha alumina and promoted with cesium (but not containing nickel) showed large silver particles after being heated in air at 600° C. for 24 hours. However, a catalyst according to the present invention comprising 8 wt % silver on an alpha alumina carrier promoted with cesium and 0.55 wt % basis nickel (present as an oxide) shows that the silver particles maintain the fine silver dispersion upon heating in air at 600° C. for 24 hours. Compare the SEM image at 5,000 magnification for the prior art (FIG. 1) and the SEM image of the catalyst according to the present invention (FIG. 2).

Therefore, the present invention provides for a catalyst for the epoxidation of an olefin wherein the catalyst exhibits improved stability. This improvement results from incorporating a nickel compound with the other promoters during the initial impregnation. This contrasts with the prior art as disclosed in U.S. Pat. No. 5,380,885, where the nickel "must be deposited on the catalyst after all of the other catalyst components have been added and after the catalyst has been at least partially dried to a degree sufficient to permit a promoting amount of nickel to be incorporated onto the catalyst" (see col. 5, lines 39-46 of the '885 patent). The current invention is better than the prior art incorporation because aqueous impregnation may be used in the present invention to add the nickel. In the '885 patent it is necessary to add the nickel compound with a solvent and the '885 patent teaches that one must avoid any aqueous impregnation.

The present invention also provides a process for preparing an epoxidation catalyst comprising depositing silver, a promoter selected from alkali metals and rhenium and a nickel compound on an alpha alumina carrier, then drying and calcining the catalyst.

The invention also provides a process for the epoxidation of an olefin comprising reacting the olefin with oxygen in the presence of an epoxidation catalyst prepared according to this invention.

Further, the invention provides a method of preparing a 1,2-diol, a 1,2-diol ether, a 1,2-carbonate, or an alkanolamine comprising obtaining an olefin oxide by the process for the epoxidation of an olefin according to this invention, and converting the olefin oxide into the 1,2-diol, the 1,2-diol ether, the 1,2-carbonate, or the alkanolamine.

DETAILED DESCRIPTION OF THE INVENTION

Figure 1:
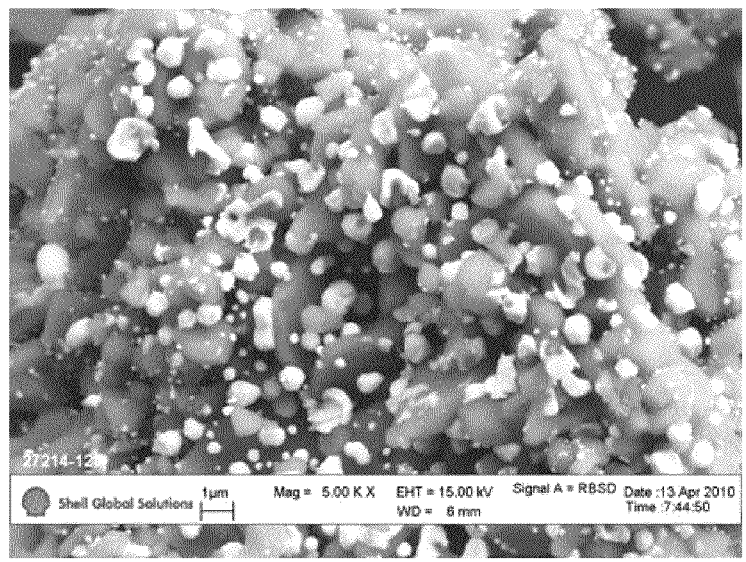
FIG. 1 is an SEM image of Catalyst A, described below, which is in the prior art.

The present invention relates to a highly selective epoxidation catalyst comprising a promoter selected from one or more of alkali metals and rhenium and a catalytically effective amount of silver as well as a nickel compound along with other optional components including other co-promoters as discussed below, where the nickel compound is present in a total quantity of nickel (measured as the metal) between 50 ppm and as high as 10 to 20 wt % based on the total catalyst. The resulting catalyst exhibits an unexpected improvement in catalytic performance: in particular a greater stability and longer usable catalyst life.

As for the carrier, there are many examples of suitable carriers as described in U.S. Pat. No. 7,714,152; US 2009/0177016; US 2009/0131695; U.S. Pat. No. 7,507,577; U.S. Pat. No. 7,507,845; US 2008/0081920; US 2009/0198076; U.S. Pat. No. 4,242,235, U.S. Pat. No. 4,740,493 and U.S. Pat. No. 4,766,105, which disclosures are herein incorporated by reference. Various carriers may be used, having a variety of pore distributions. The following are some of the many options for carrier pore distribution:

- carrier having a surface area of at least 1 $m^2/g$, and a pore size distribution such that pores with diameters in the range of from 0.2 to 10 μm represent at least 70% of the total pore volume and such pores together provide a pore volume of at least 0.27 ml/g, relative to the weight of the carrier.
- carrier having a median pore diameter of more than 0.5 μm, and a pore size distribution wherein at least 80% of the total pore volume is contained in pores with diameters in the range of from 0.1 to 10 μm and at least 80% of the pore volume contained in the pores with diameters in the range of from 0.1 to 10 μm is contained in pores with diameters in the range of from 0.3 to 10 μm.
- carrier having at least two log differential pore volume distribution peaks in a pore diameter range of 0.01-100 μm and at least one peak of the above peaks is present in a pore diameter range of 0.01-1.0 μm in the pore size distribution measured by mercury porosimetry, wherein each peak is a maximum value of the log differential pore volume distribution of 0.2 $cm^3/g$ or larger.
- carrier having a bimodal pore size distribution, with a first mode of pores which has a mean diameter ranging from about 0.01 m to about 5 μm, and a second mode of pores which has a mean diameter ranging from about 5 μm to about 30 μm.
- carrier having a pore volume from pores with less than 1 micron in diameter of less than 0.20 ml/g, a pore volume from pores with greater than 5 micron in diameter of less than 0.20 ml/g, and a pore volume from pores between 1 micron in diameter and 5 microns in diameter at least 40 percent of a total pore volume.

In certain embodiments of this invention, the carrier exhibits non-platelet morphology. As used herein, the term "non-platelet morphology" refers to the morphology of the carrier when imaged by scanning electron microscopy at a magnification of 2000, and to the substantial absence in such images of structures having substantially flat surfaces. By "substantial absence" of such structures it is meant that at most 25% of the structures have a substantially flat surface. By "substantially flat" it is meant that the radius of the curvature of the surface is at least 2 times the length of the largest dimension of the surface. The structures having a substantially flat surface have typically an aspect ratio of at most 4:1, the aspect ratio of a structure being the ratio of the largest dimension to the smallest dimension of the structure. The term "structures" refers to structural entities in the carrier which can be designated to represent individual particles of carrier material fused or bonded together to form the carrier.

The carrier may be based on a wide range of materials. Such materials may be natural or artificial inorganic materials and they may include refractory materials, silicon carbide, clays, zeolites, charcoal and alkaline earth metal carbonates, for example calcium carbonate. Preferred are refractory materials, such as alumina, magnesia, zirconia and silica. The most preferred material is α-alumina. Typically, the carrier comprises at least 85 weight percent, more typically at least 90 weight percent α-alumina.

Carriers may generally be made by firing particulate components at an elevated temperature until the particles sinter together. In general, firing may be continued until the particles are bonded together, either by the formation of bonds from any added bond material or through sintering, but preferably not beyond the point at which the water absorption of the carrier is reduced.

Burnout materials may or may not be used in the firing process. Burnout materials are well known in the art (cf., for example, F F Y Wang (Ed.), "Treatise on Materials Science and Technology", Volume 9, (New York, 1976), pp. 79-81; or J S Reed, "Introduction to the Principles of Ceramic Processing", (New York, 1988), pp. 152 ff.). The burnout materials may be used to enhance preservation of the structure during a green, i.e. unfired, phase of the carrier preparation, for example the phase in which formed bodies are shaped, for example by extrusion. The burnout materials are removed during the firing. The use of burnout materials also allows more complete sintering without too great a reduction in water absorption of the carrier. The burnout materials are typically finely divided solid organic materials that volatilize or burn, leaving as little residue as possible.

It is also a common expedient to use a bond material, i.e. a material which reduces the length of sintering time applied to bond the particles together. The bond material may also form a coating on at least a part of the carrier surface, which makes the carrier surface more receptive. The bond material may be based on a silica-containing composition comprising a crystallization inhibitor, inhibiting the formation of crystalline silica-containing compositions.

The silica-containing compositions for use as a bond material may comprise an alkali metal silicate bond material, or preferably an alkaline earth metal silicate bond material. The bond material may further comprise a hydrated alumina and optionally a titanium component and/or a zirconium component.

It has been found that, suitably, alumina carriers for use in this invention may be made by a method which comprises forming a mixture of different particulate α-alumina and optionally in addition an alkaline earth metal silicate bond material; and then shaping the mixture into formed bodies and firing the formed bodies, typically at a temperature of from 1200 to 1550° C., to form the carrier.

The alumina particles are readily commercially available, or they may readily be made, for example, by subjecting more coarse materials to grinding and sieving operations. In an embodiment, the smaller particles may be prepared from the larger particles by grinding, and the ground and un-ground particles are then combined. In another embodiment, the desired mixture of large and small particles may be formed by grinding relatively large particles to the extent that the mixture of particles has the desired bimodal particle size distribution.

The alkaline earth metal silicate bond material may comprise an alkaline earth metal silicate, for example calcium silicate or, preferably, magnesium silicate. The alkaline earth metal silicate can also be in the form of natural materials such as talc, serpentine, pyroxene, amphibole, and olivine. Alternatively to or in addition to the alkaline earth metal silicate, the alkaline earth metal silicate bond material may comprise a combination of an alkaline earth metal compound and a silica compound. Suitable alkaline earth metal compounds are alkaline earth metal salts, for example nitrates, acetates, lactates, citrates, oxalates, oxides, carbonates or sulfates, in particular magnesium nitrate or magnesium acetate. Suitable silica compounds are silica sol, precipitated silica, amorphous silica, amorphous alkali metal silica, or amorphous alkali metal aluminosilicate. Amorphous silica compounds are preferred. The quantity of alkaline earth metal silicate bond material may suitably be in the range of from 0.2 to 10 weight percent, calculated as the total weight of alkaline earth metal oxide and silicate, as $SiO_2$, relative to the total weight of α-alumina in the mixture.

The alkaline earth metal silicate bond material may or may not comprise, as an additional component, a hydrated alumina. A suitable hydrated alumina is, for example, gibbsite, bayerite or diaspore. A preferred hydrated alumina is boehmite. The quantity of the hydrated alumina may suitably be in the range of from 0.1 to 15 weight percent, preferably from 0.2 to 10 weight percent, calculated as the weight of aluminum oxide, $Al_2O_3$, relative to the total weight of α-alumina in the mixture.

The alkaline earth metal silicate bond material may or may not comprise, as an additional component, a zirconium component, as a solid component or as a liquid component. Suitable zirconium components are zirconium dioxide and zirconium compounds which convert to zirconium dioxide upon firing. Such zirconium compounds may be salts, such as zirconyl nitrate, zirconyl sulfate or basic zirconyl carbonate. The quantity of the zirconium component may suitably be in the range of from 0 to 10 weight percent, more suitably from 0.2 to 5 weight percent, calculated as the weight of zirconium dioxide, $ZrO_2$, relative to the total weight of α-alumina in the mixture.

The alkaline earth metal silicate bond material may or may not comprise, as an additional component, a titanium component. Suitable titanium components are titanium dioxide, titanyl sulfate, titanyl oxalate, titanyl chloride, organo titanates, and other compounds which convert to titanium dioxide upon firing. Hydrated aluminas may in some instances be contaminated with titanium compounds and act as a source of the titanium component. The quantity of the titanium component may suitably be in the range of from 0 to 5 weight percent, more suitably from 0 to 1 weight percent, calculated as the weight of titanium dioxide, $TiO_2$, relative to the total weight of α-alumina in the mixture. In an embodiment, the alkali metal silicate bond material may comprise an alkali metal silicate, for example amorphous sodium or lithium silicate.

Burnout materials may be selected from the group of polypropylenes, polyethylenes, carbohydrates, gums, flours, proteins, lignins, resins, waxes, alcohols, and esters. When preparing an α-alumina carrier, the quantity of burnout material may suitably be in the range of from 0.2 to 10 weight percent, more suitably from 0.5 to 5 weight percent, relative to the total weight of α-alumina in the mixture. The selection of the burnout material is considered not to be of any criticality to the invention. Also, in the practice of this invention using an α-alumina carrier, no burnout material may be used in the preparation of the carrier.

It is also preferred that the carrier particles be prepared in the form of formed bodies, the size of which is in general determined by the dimensions of an epoxidation reactor in which they are to be deposited. Generally however it is found very convenient to use particles such as formed bodies in the form of powder, trapezoidal bodies, cylinders, saddles, spheres, doughnuts, and the like. The cylinders may be solid or hollow, straight or bent, and they may have their length and cross-sectional dimensions about the same and from 5 to 10 mm. Preferably the cylinders are hollow with a wall thickness of about 1 to 4 mm.

The formed bodies may be dried and fired at a temperature high enough to ensure that the alumina particles are joined together by a sintering action and/or by the formation of bonds formed from the bond material, if incorporated in the mixture. Generally, drying may take place between 20 and 400° C. and preferably between 30 and 300° C., typically for a period of up to 100 hours and preferably from 5 minutes to 50 hours. Typically, drying is performed to the extent that the mixture contains less than 2 weight percent of water. Generally, firing may take place at a temperature of at least 1200° C., preferably between 1250 and 1550° C., typically for a period of up to about 8 hours and preferably from 2 to 6 hours. Drying and firing may be carried out in any atmosphere, such as in air, nitrogen, or helium, or mixtures thereof. Preferably, in particular when the formed bodies contain organic material, the firing is at least in part or entirely carried out in an oxidizing atmosphere, such as in an oxygen-containing atmosphere.

The formed bodies may be dried and fired at a temperature high enough to ensure that the alumina particles are joined together by a sintering action and/or by the formation of bond posts formed from the bond material, if incorporated in the mixture. Generally, drying may take place between 20 and 400° C. and preferably between 30 and 300° C., typically for a period of up to 100 hours and preferably from 5 minutes to 50 hours. Typically, drying is performed to the extent that the mixture contains less than 2 weight percent of water. Generally, firing may take place at a temperature of at least 1200° C., preferably between 1250 and 1550° C., typically for a period of up to about 8 hours and preferably from 2 to 6 hours. Drying and firing may be carried out in any atmosphere, such as in air, nitrogen, or helium, or mixtures thereof. Preferably, in particular when the formed bodies contain organic material, the firing is at least in part or entirely carried out in an oxidizing atmosphere, such as in an oxygen-containing atmosphere.

The performance of the catalyst may be enhanced if the carrier is washed, to remove soluble residues, before deposition of other catalyst ingredients on the carrier. On the other hand, unwashed carriers may also be used successfully. A useful method for washing the carrier comprises washing the carrier in a continuous fashion with hot, demineralised water, until the electrical conductivity of the effluent water does not further decrease. A suitable temperature of the demineralised water is in the range of 80 to 100° C., for example 90° C. or 95° C. Reference may be made to WO-00/15333 and U.S. Pat. No. 6,368,998, which are incorporated herein by reference.

Preparation of Silver Catalyst

The preparation of the silver catalyst is known in the art and the known methods are applicable to the preparation of the catalyst which may be used in the practice of this invention. In general terms, the impregnation process comprises impregnating the support with one or more solutions comprising silver, rhenium and nickel promoter, then drying the impregnated support. The essence of the present invention is the incorporation of one or more nickel compounds or nickel complexes in the initial impregnation of the catalyst, along with the silver, rhenium and other co-promoters. The term "initial impregnation" refers to impregnation in a single or multiple steps, prior to any drying of the impregnated catalyst.

As used in the instant specification and claims, the terminology "impregnating the support with one or more solutions comprising silver, a promoter selected from alkali metals and rhenium and nickel promoter", and similar or cognate terminology means that the support is impregnated in a single or multiple impregnation with one solution containing silver, alkali metal, rhenium and nickel promoter in differing amounts; or in multiple impregnations with two or more solutions, wherein each solution contains at least one component selected from silver, alkali metal, rhenium and nickel promoter, with the proviso that all of the components of silver, will individually be found in at least one of the solutions. In addition, there may be other rhenium co-promoters as discussed further below.

Methods of depositing silver on the carrier include impregnating the carrier or carrier bodies with a silver compound containing cationic silver and/or complexed silver and performing a reduction to form metallic silver particles. For further description of such methods, reference may be made to U.S. Pat. No. 5,380,697, U.S. Pat. No. 5,739,075, U.S. Pat. No. 4,766,105, and U.S. Pat. No. 6,368,998, which are incorporated herein by reference. Suitably, silver dispersions, for example silver sols, may be used to deposit silver on the carrier.

The reduction of cationic silver to metallic silver may be accomplished during a step in which the catalyst is dried, so that the reduction as such does not require a separate process step. This may be the case if the silver containing impregnation solution comprises a reducing agent, for example, an oxalate, a lactate or formaldehyde.

Appreciable catalytic activity is obtained by employing a silver content of the catalyst of at least 10 g/kg, relative to the weight of the catalyst. Preferably, the catalyst comprises silver in a quantity of from 10 to 500 g/kg, more preferably from 50 to 450 g/kg. As used herein, unless otherwise specified, the weight of the catalyst is deemed to be the total weight of the catalyst including the weight of the carrier and catalytic components.

The catalyst for use in this invention may additionally comprise a rhenium promoter component deposited on the carrier in a quantity of greater than 1 mmole/kg, relative to the weight of the catalyst. Preferably, the rhenium promoter may be present in a quantity of at least 1.25 mmole/kg. Preferably, the rhenium promoter may be present in a quantity of at most 500 mmole/kg, more preferably at most 50 mmole/kg. The form in which the rhenium promoter may be deposited onto the carrier is not material to the invention. For example, the rhenium promoter may suitably be provided as an oxide or as an oxyanion, for example, as a rhenate or perrhenate, in salt or acid form.

The essence of the present invention is the incorporation of a nickel compound or nickel complex as a promoter during the initial impregnation. Nickel can be deposited in the form of salts, complexes and the like but it is believed that during the catalyst drying and heating step it is decomposed to oxides. Nickel is not believed to be present in the metallic state on the final catalyst. As used herein, the term "nickel compounds" refers to the use of one or more compounds of nickel, as appropriate, to provide a promoting effect. In a preferred embodiment, the nickel compound is selected from the group consisting of nickel carbonate, nickel nitrate, nickel acetate, nickel acetylacetonate, nickel chloride, nickel sulfate and mixtures thereof, with nickel carbonate, nickel nitrate, nickel sulfate and mixtures thereof being particularly preferred. Particularly preferred nickel promoters are nickel carbonate and nickel nitrate. "Nickel complexes" are possible with the addition of amines or ammonia. These amine or ammonia complexes are particularly preferred as they are stable, miscible and compatible with the silver solution containing ammonia or amines as silver complexing agents.

The amount of nickel compound or nickel complex added is an amount that results in greater stability for the catalyst. Preferably the amount is at least 50 ppmw, based on the weight of the entire catalyst and measured as nickel metal (the nickel will be present on the catalyst as an oxide). The amount of nickel present based on the nickel metal content alone is preferably between 50 ppm and 20 weight percent. Preferred amounts are 50 ppm to 10 weight percent.

The catalysts for use in this invention may also comprise an alkali metal promoter. Preferably, the alkali metals are selected from lithium, potassium, rubidium and cesium. Most preferably, the alkali metal is lithium, potassium and/or cesium. Preferably, the alkali metal element may be present in the catalyst in a total quantity of from 0.01 to 500 mmole/kg. The further element may be provided in any form. For example, salts or hydroxides of an alkali metal are suitable. For example, lithium compounds may be lithium hydroxide or lithium nitrate.

The catalyst for use in this invention may optionally comprise a first co-promoter component. The first co-promoter may be selected from sulfur, phosphorus, boron, and mixtures thereof. It is particularly preferred that the first co-promoter comprises, as an element, sulfur.

The catalyst for use in this invention may additionally comprise a second co-promoter component. The second co-promoter component may be selected from tungsten, molybdenum, chromium, and mixtures thereof. It is particularly preferred that the second co-promoter component comprises, as an element, tungsten and/or molybdenum, in particular tungsten. The form in which first co-promoter and second co-promoter components may be deposited onto the carrier is not material to the invention. For example, the first co-promoter and second co-promoter components may suitably be provided as an oxide or as an oxyanion, for example, as a tungstate, molybdate, or sulfate, in salt or acid form.

The total quantity of the first co-promoter and the second co-promoter deposited on the carrier is at most 20.0 mmole/kg, calculated as the total quantity of the elements (i.e., the total of sulfur, phosphorous, boron, tungsten, molybdenum and/or chromium) relative to the weight of the catalyst.

In an embodiment, the molar ratio of the first co-promoter to the second co-promoter may be greater than 1. The molar ratio of the first co-promoter to the second co-promoter may be at most 20.

In an embodiment, the molar ratio of the rhenium promoter to the second co-promoter may be greater than 1. The molar ratio of the rhenium promoter to the second co-promoter may be at most 20, preferably at most 15, more preferably at most 10.

The catalyst may preferably also comprise a further element deposited on the carrier. Eligible further elements may be selected from nitrogen, fluorine, alkaline earth metals, titanium, hafnium, zirconium, vanadium, thallium, thorium, tantalum, niobium, gallium, germanium, and mixtures thereof. Preferably, the alkaline earth metals are selected from calcium, magnesium and barium. Preferably, the further element may be present in the catalyst in a total quantity of from 0.01 to 500 mmole/kg. The further element may be provided in any form. For example, salts or hydroxides of an alkaline earth metal are suitable.

It is important to select a target value for potassium for the entire catalyst composition (carrier plus added catalyst components). For example if the target water extractable quantity of potassium is 10 mmole/g, relative to the weight of the catalyst, such target potassium level is achieved by measuring the potassium level of the carrier and adding sufficient additional potassium during the catalyst impregnation to achieve the target potassium level. A similar process for adding sodium could be applied in order to achieve the proper target level. Lithium and cesium could be treated the same way, except that they are not typically present as impurities in the carrier. If they did, one could use the same procedure for the target.

The quantity of water extractable potassium in the catalyst is deemed to be the quantity insofar as it can be extracted from the catalyst. The extraction involves extracting a 2-gram sample of the catalyst three times by heating it in 25-gram portions of de-ionized water for 5 minutes at 100° C. and determining in the combined extracts the amount of potassium by using a known method, for example atomic absorption spectroscopy.

As used herein, unless otherwise specified, the quantity of alkali metal present in the catalyst and the quantity of water leachable components present in the carrier are deemed to be the quantity insofar as it can be extracted from the catalyst or carrier with de-ionized water at 100° C. The extraction method involves extracting a 10-gram sample of the catalyst or carrier three times by heating it in 20 ml portions of de-ionized water for 5 minutes at 100° C. and determining in the combined extracts the relevant metals by using a known method, for example atomic absorption spectroscopy.

As used herein, unless otherwise specified, the quantity of alkaline earth metal present in the catalyst and the quantity of acid leachable components present in the carrier are deemed to be the quantity insofar as it can be extracted from the catalyst or carrier with 10% w nitric acid in de-ionized water at 100° C. The extraction method involves extracting a 10-gram sample of the catalyst or carrier by boiling it with a 100 ml portion of 10% w nitric acid for 30 minutes (1 atm., i.e. 101.3 kPa) and determining in the extract the concentrations of relevant metals by using a known method, for example atomic absorption spectroscopy. Reference is made to U.S. Pat. No. 5,801,259, which is incorporated herein by reference.

Epoxidation Process

Although the present epoxidation process may be carried out in many ways, it is preferred to carry it out as a gas phase process, i.e. a process in which the feed is contacted in the gas phase with the catalyst which is present as a solid material, typically in a packed bed. Generally the process is carried out as a continuous process.

The olefin for use in the present epoxidation process may be any olefin, such as an aromatic olefin, for example styrene, or a di-olefin, whether conjugated or not, for example 1,9-decadiene or 1,3-butadiene. Typically, the olefin is a mono-olefin, for example 2-butene or isobutene. Preferably, the olefin is a mono-α-olefin, for example 1-butene or propylene. The most preferred olefin is ethylene. Suitably, mixtures of olefins may be used.

The quantity of olefin present in the feed may be selected within a wide range. Typically, the quantity of olefin present in the feed will be at most 80 mole-%, relative to the total feed. Preferably, it will be in the range of from 0.5 to 70 mole-%, in particular from 1 to 60 mole-%, on the same basis. As used herein, the feed is considered to be the composition which is contacted with the catalyst.

The present epoxidation process may be air-based or oxygen-based, see "Kirk-Othmer Encyclopedia of Chemical Technology", $3^{rd}$ edition, Volume 9, 1980, pp. 445-447. In the air-based process, air or air enriched with oxygen is employed as the source of the oxidizing agent while in the oxygen-based processes high-purity (at least 95 mole-%) or very high purity (at least 99.5 mole-%) oxygen is employed as the source of the oxidizing agent. Reference may be made to U.S. Pat. No. 6,040,467, incorporated by reference, for further description of oxygen-based processes. Presently most epoxidation plants are oxygen-based and this is a preferred embodiment of the present invention.

The quantity of oxygen present in the feed may be selected within a wide range. However, in practice, oxygen is generally applied in a quantity which avoids the flammable regime. Typically, the quantity of oxygen applied will be within the range of from 1 to 15 mole-%, more typically from 2 to 12 mole-% of the total feed.

In order to remain outside the flammable regime, the quantity of oxygen present in the feed may be lowered as the quantity of the olefin is increased. The actual safe operating ranges depend, along with the feed composition, also on the reaction conditions such as the reaction temperature and the pressure.

A reaction modifier may be present in the feed for increasing the selectively, suppressing the undesirable oxidation of olefin or olefin oxide to carbon dioxide and water, relative to the desired formation of olefin oxide. Many organic compounds, especially organic halides and organic nitrogen compounds, may be employed as the reaction modifiers. Nitrogen oxides, organic nitro compounds such as nitromethane, nitroethane, and nitropropane, hydrazine, hydroxylamine or ammonia may be employed as well. It is frequently considered that under the operating conditions of olefin epoxidation the nitrogen-containing reaction modifiers are precursors of nitrates or nitrites, i.e. they are so-called nitrate- or nitrite-forming compounds. Reference may be made to EP-A-3642 and U.S. Pat. No. 4,822,900, which are incorporated herein by reference, for further description of nitrogen-containing reaction modifiers.

Organic halides are the preferred reaction modifiers, in particular organic bromides, and more in particular organic chlorides. Preferred organic halides are chlorohydrocarbons or bromohydrocarbons. More preferably they are selected from the group of methyl chloride, ethyl chloride, ethylene dichloride, ethylene dibromide, vinyl chloride or a mixture thereof. Most preferred reaction modifiers are ethyl chloride, vinyl chloride and ethylene dichloride.

Suitable nitrogen oxides are of the general formula $NO_x$ wherein x is in the range of from 1 to 2, and include for example NO, $N_2O_3$ and $N_2O_4$. Suitable organic nitrogen compounds are nitro compounds, nitroso compounds, amines, nitrates and nitrites, for example nitromethane, 1-nitropropane or 2-nitropropane. In preferred embodiments, nitrate- or nitrite-forming compounds, e.g. nitrogen oxides and/or organic nitrogen compounds, are used together with an organic halide, in particular an organic chloride.

The reaction modifiers are generally effective when used in small quantities in the feed, for example up to 0.1 mole-%, relative to the total feed, for example from $0.01 \times 10^{-4}$ to 0.01 mole-%. In particular when the olefin is ethylene, it is preferred that the reaction modifier is present in the feed in a quantity of from $0.1 \times 10^{-4}$ to $500 \times 10^{-4}$ mole-%, in particular from $0.2 \times 10^{-4}$ to $200 \times 10^{-4}$ mole-%, relative to the total feed.

In addition to the olefin, oxygen and the reaction modifier, the feed may contain one or more optional components, such as carbon dioxide, inert gases and saturated hydrocarbons. Carbon dioxide is a by-product in the epoxidation process. However, carbon dioxide generally has an adverse effect on the catalyst activity. Typically, a quantity of carbon dioxide in the feed in excess of 25 mole-%, preferably in excess of 10 mole-%, relative to the total feed, is avoided. A quantity of carbon dioxide of less than 3 mole-%, preferably less than 2 mole-%, in particular in the range of from 0.3 to less than 1 mole-%, relative to the total feed, may be employed. Under commercial operations, a quantity of carbon dioxide of at least 0.1 mole-%, or at least 0.2 mole-%, relative to the total feed, may be present in the feed. Inert gases, for example nitrogen or argon, may be present in the feed in a quantity of from 30 to 90 mole-%, typically from 40 to 80 mole-%. Suitable saturated hydrocarbons are methane and ethane. If saturated hydrocarbons are present, they may be present in a quantity of up to 80 mole-%, relative to the total feed, in particular up to 75 mole-%. Frequently, they are present in a quantity of at least 30 mole-%, more frequently at least 40 mole-%. Saturated hydrocarbons may be added to the feed in order to increase the oxygen flammability limit.

The epoxidation process may be carried out using reaction temperatures selected from a wide range. Preferably the reaction temperature is in the range of from 150 to 325° C., more preferably in the range of from 180 to 300° C.

The epoxidation process is preferably carried out at a reactor inlet pressure in the range of from 1000 to 3500 kPa. "GHSV" or Gas Hourly Space Velocity is the unit volume of gas at normal temperature and pressure (0° C., 1 atm, i.e. 101.3 kPa) passing over one unit volume of packed catalyst per hour. Preferably, when the epoxidation process is a gas phase process involving a packed catalyst bed, the GHSV is in the range of from 1500 to 10000 Nl/(l·h). Preferably, the process is carried out at a work rate in the range of from 0.5 to 10 kmole olefin oxide produced per $m^3$ of catalyst per hour, in particular 0.7 to 8 kmole olefin oxide produced per $m^3$ of catalyst per hour, for example 5 kmole olefin oxide produced per $m^3$ of catalyst per hour. As used herein, the work rate is the amount of the olefin oxide produced per unit volume of catalyst per hour and the selectivity is the molar quantity of the olefin oxide formed relative to the molar quantity of the olefin converted. Suitably, the process is conducted under conditions where the olefin oxide partial pressure in the product mix is in the range of from 5 to 200 kPa, for example 11 kPa, 27 kPa, 56 kPa, 77 kPa, 136 kPa, and 160 kPa. The term "product mix" as used herein is understood to refer to the product recovered from the outlet of an epoxidation reactor.

The olefin oxide produced may be recovered from the product mix by using methods known in the art, for example by absorbing the olefin oxide from a reactor outlet stream in water and optionally recovering the olefin oxide from the aqueous solution by distillation. At least a portion of the aqueous solution containing the olefin oxide may be applied in a subsequent process for converting the olefin oxide into a 1,2-diol, a 1,2-diol ether, a 1,2-carbonate, or an alkanolamine.

Conversion of Olefin Oxide to Other Chemicals

The olefin oxide produced in the epoxidation process may be converted into a 1,2-diol, a 1,2-diol ether, a 1,2-carbonate, or an alkanolamine. As this invention leads to a more attractive process for the production of the olefin oxide, it concurrently leads to a more attractive process which comprises producing the olefin oxide in accordance with the invention and the subsequent use of the obtained olefin oxide in the manufacture of the 1,2-diol, 1,2-diol ether, 1,2-carbonate, and/or alkanolamine.

The conversion into the 1,2-diol or the 1,2-diol ether may comprise, for example, reacting the olefin oxide with water, suitably using an acidic or a basic catalyst. For example, for making predominantly the 1,2-diol and less 1,2-diol ether, the olefin oxide may be reacted with a ten fold molar excess of water, in a liquid phase reaction in presence of an acid catalyst, e.g. 0.5-1.0% w sulfuric acid, based on the total reaction mixture, at 50-70° C. at 1 bar absolute, or in a gas phase reaction at 130-240° C. and 20-40 bar absolute, preferably in the absence of a catalyst. The presence of such a large quantity of water may favor the selective formation of 1,2-diol and may function as a sink for the reaction exotherm, helping control the reaction temperature. If the proportion of water is lowered, the proportion of 1,2-diol ethers in the reaction mixture is increased. The 1,2-diol ethers thus produced may be a di-ether, tri-ether, tetra-ether or a subsequent ether. Alternative 1,2-diol ethers may be prepared by converting the olefin oxide with an alcohol, in particular a primary alcohol, such as methanol or ethanol, by replacing at least a portion of the water by the alcohol.

The olefin oxide may be converted into the corresponding 1,2-carbonate by reacting the olefin oxide with carbon dioxide. If desired, a 1,2-diol may be prepared by subsequently reacting the 1,2-carbonate with water or an alcohol to form the 1,2-diol. For applicable methods, reference is made to U.S. Pat. No. 6,080,897, which is incorporated herein by reference.

The conversion into the alkanolamine may comprise, for example, reacting the olefin oxide with ammonia. Anhydrous ammonia is typically used to favor the production of monoalkanolamine. For methods applicable in the conversion of the olefin oxide into the alkanolamine, reference may be made to, for example U.S. Pat. No. 4,845,296, which is incorporated herein by reference.

The 1,2-diol and the 1,2-diol ether may be used in a large variety of industrial applications, for example in the fields of food, beverages, tobacco, cosmetics, thermoplastic polymers, curable resin systems, detergents, heat transfer systems, etc. The 1,2-carbonates may be used as a diluent, in particular as a solvent. Alkanolamines may be used, for example, in the treating ("sweetening") of natural gas.

Unless specified otherwise, the low-molecular weight organic compounds mentioned herein, for example the olefins, 1,2-diols, 1,2-diol ethers, 1,2-carbonates, alkanolamines, and reaction modifiers, have typically at most 40 carbon atoms, more typically at most 20 carbon atoms, in particular at most 10 carbon atoms, more in particular at most 6 carbon atoms. As defined herein, ranges for numbers of carbon atoms (i.e. carbon number) include the numbers specified for the limits of the ranges.

Having generally described the invention, a further understanding may be obtained by reference to the following examples, which are provided for purposes of illustration only and are not intended to be limiting unless otherwise specified.

Example 1

Preparation of Stock Silver Solution

This example describes the preparation of a stock silver impregnation solution used in preparing Catalysts A and B in Example 2.

A silver-amine-oxalate stock solution was prepared by the following procedure:

In a 5-liter stainless steel beaker, 415 g of reagent-grade sodium hydroxide were dissolved in 2340 ml de-ionized water, and the temperature was adjusted to 50° C.

In a 4-liter stainless steel beaker, 1699 g high purity "Spectropure" silver nitrate was dissolved in 2100 ml de-ionized water, and the temperature was adjusted to 50° C.

The sodium hydroxide solution was added slowly to the silver nitrate solution, with stirring, while maintaining a solution temperature of 50° C. This mixture was stirred for 15 minutes. The pH of the solution was maintained at above 10 by the addition of sodium hydroxide solution as required.

Water was removed from the precipitate created in the mixing step and the conductivity of the water, which contained sodium and nitrate ions, was measured. An amount of fresh deionized water equal to the amount removed was added back to the silver solution. The solution was stirred for 15 minutes at 40° C. The process was repeated until the conductivity of the water removed was less than 90 μmho/cm. 1500 ml fresh deionized water was then added. 630 g of high-purity oxalic acid dihydrate were added in approximately 100 g increments. The temperature was kept at 40° C. (±5° C.) and the pH of the solution was monitored during the addition of the last 130 grams of oxalic acid dihydrate to ensure that the pH did not drop below 7.8 for an extended period of time.

Water was removed from this mixture to leave a highly concentrated silver-containing slurry. The silver oxalate slurry was cooled to 30° C.

699 g of 92 weight percent ethylenediamine (8% de-ionized water) was added while maintaining a temperature no greater than 30° C. The final solution was used as a stock silver impregnation solution for preparing Catalysts A and B.

Example 2

Preparation of Catalysts

The carrier used was alpha alumina with the following properties: water absorption, 49.8 cc/100 g, bulk packing density, 50.2 lb/ft$^3$, surface area 0.74 m$^2$/g. Carrier composition was >98% alpha alumina, 1% $ZrO_2$ and less the 1% magnesium silicate The carrier has a bimodal pore size distribution. It is believed that mono-modal, bi-modal or multiple mode carriers with pores larger than 0.1 micron are suitable for the invention.

Catalyst A. Comparative Example, No Nickel 50 grams of silver solution of specific gravity 1.573, containing 30.4% Ag, ethylenediamine and oxalic acid in a 2:2:1 molar ratio was mixed with 0.1919 grams of CsOH solution containing 47.02% Cs. To this was added 30 grams of solid carrier pellets. Pellets were in a shape of hollow cylinders with 8.5 external diameter, 8.5 mm height and 3.5 mm internal bore. Pellets and solution were evacuated for 5 minutes after which time the vacuum was broken and pellets were decanted from the excess of solution. The pellets were then centrifuged for 2 min at 275 rpm. The catalyst was then dried in a flowing air at 250° C. for 8 minutes. During this drying step silver is reduced to metallic silver. The catalyst contained 8% Ag.

Catalyst B. According to the Invention, Promoted with Nickel 204 grams of silver solution of specific gravity 1.573, containing 30.4% Ag, ethylenediamine and oxalic acid in a 2:2:1 molar ratio was mixed with Ni complex prepared by mixing 9.85 g of nickel nitrate hexahydrate and 54 grams of ethylenediamine/water mixture (1:1 W/W). 50 grams of this solution was taken and mixed with 0.1919 grams of CsOH solution containing 47.02% Cs. To this was added 30 grams of solid carrier pellets. Pellets were in a shape of hollow cylinders with 8.5 diameter, 8.5 mm height and 3.5 mm internal bore. Pellets and solution were evacuated for 5 minutes after which time the vacuum was broken and pellets were decanted from the excess of solution. The pellets were then centrifuged for 2 min at 275 rpm. The catalyst was then dried in a flowing air at 250° C. for 8 minutes. During this drying step silver is reduced to metallic silver. The catalyst contained 8% Ag and 0.55% Ni (as expressed on metal basis).

Example 3

Accelerated Aging Test

Figure 2:
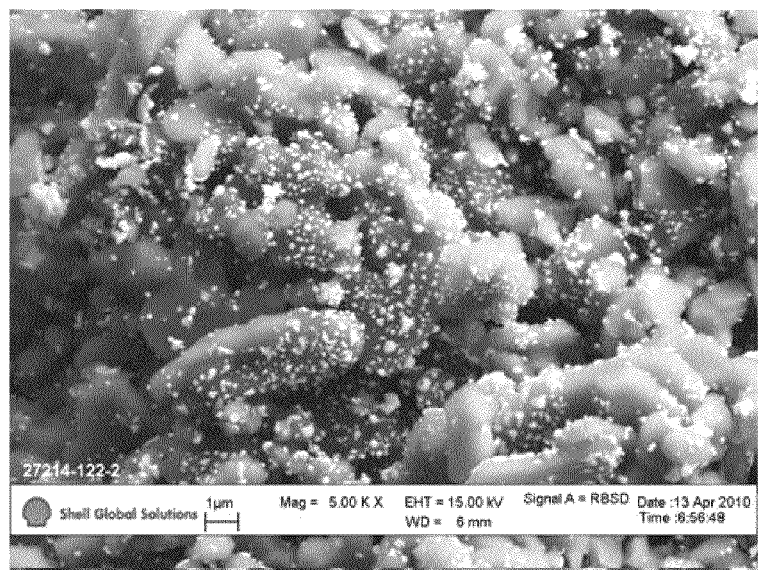
FIG. 2 is an SEM of Catalyst B, described below, which is a catalyst made according to the claimed invention.

Both Catalyst A and Catalyst B were subjected to an accelerated aging test by placing portions in ceramic dishes and subjecting them to heating in an oven in air at a temperature of 600° C. for 24 hours. After cooling, SEM photographs were taken of both catalysts. FIG. 1 is an SEM image of heat treated Catalyst A (according to the prior art) at 5,000 magnification. As shown in the figure, the silver particles have agglomerated and are significantly larger in size than the fresh catalyst. FIG. 2 is an SEM image of heat treated Catalyst B (according to the invention) at 5,000 magnification. As shown in the figure, the silver has maintained fine silver dispersion.

Accordingly, sintering is reduced significantly with the use of the invention claimed herein, resulting in improved stability and longer usable catalyst life.

What is claimed is:

1. A process for preparing a catalyst for the epoxidation of an olefin comprising: depositing on a carrier during an initial impregnation, (i) silver, (ii) a promoting amount of one or more promoters selected from the group consisting of alkali metals and rhenium, and (iii) a promoting amount of nickel, wherein the nickel is added as a nickel compound or complex containing nickel.

2. The process as claimed in claim 1, wherein the silver is present in an amount of 10 to 500 g/kg, relative to the weight of the catalyst.

3. The process as claimed in claim 1, wherein the nickel is added as a nickel compound that is selected from the group consisting of nickel carbonate, nickel nitrate, nickel acetate, nickel acetylacetonate, nickel chloride, nickel sulfate and mixtures thereof.

4. The process as claimed in claim 3, wherein the quantity of the nickel compound is between 50 ppmw and 20 wt %, expressed as nickel metal, relative to the weight of the catalyst.

5. The process as claimed in claim 1, wherein the nickel is added as a complex with one selected from the group consisting of ammonia, an organic amine, and mixtures thereof.

6. The process as claimed in claim 1, wherein the one or more promoters comprises rhenium and the promoting amount is at least 1 mmole/kg, relative to the weight of the catalyst.

7. The process as claimed in claim 1, wherein the one or more promoters comprises an alkali metal selected from the group consisting of lithium, potassium, cesium and mixtures thereof.

8. The process as claimed in claim 1 further comprising depositing on the carrier a first co-promoter during the initial impregnation, wherein the first co-promoter is selected from the group consisting of sulfur, phosphorus, boron, and mixtures thereof.

9. The process as claimed in claim 8 further comprising depositing on the carrier a second co-promoter during the initial impregnation, wherein the second co-promoter is selected from the group consisting of tungsten, molybdenum, chromium, and mixtures thereof.

* * * * *